United States Patent [19]

Ries et al.

[11] Patent Number: 5,549,688
[45] Date of Patent: Aug. 27, 1996

[54] ASYMMETRIC FEMORAL PROSTHESIS

[75] Inventors: Michael Ries, Cooperstown, N.Y.; Brian Schumacher, Cordova, Tenn.

[73] Assignee: Smith & Nephew Richards Inc., Memphis, Tenn.

[21] Appl. No.: 285,917

[22] Filed: Aug. 4, 1994

[51] Int. Cl.$^6$ ........................................ A61F 2/38
[52] U.S. Cl. ........................................ 623/20
[58] Field of Search ........................................ 623/20, 18

[56] References Cited

U.S. PATENT DOCUMENTS

| | | | |
|---|---|---|---|
| 4,081,866 | 4/1978 | Upshaw | 623/20 |
| 4,865,606 | 9/1989 | Rehder | 623/20 |
| 5,047,057 | 9/1991 | Lawes | 623/20 |
| 5,133,758 | 7/1992 | Hollister | 623/20 |
| 5,133,759 | 7/1992 | Turner | 623/20 |
| 5,282,870 | 2/1994 | Moser et al. | 623/20 |
| 5,314,483 | 5/1994 | Wehrli et al. | 623/20 |
| 5,326,361 | 7/1994 | Hollister | 623/20 |

FOREIGN PATENT DOCUMENTS

| | | | |
|---|---|---|---|
| 719625 | 3/1980 | U.S.S.R. | 623/20 |
| 8603117 | 6/1986 | WIPO | 623/20 |

OTHER PUBLICATIONS

"Femoral Implant" (single sheet).
"The Technique of Total Knee Arthroplasty–Intraoperative Alignment and Instrumentation", pp. 130–133.
"Genesis Total Knee System", Smith & Nephew Richards Publication on Surgical Technique.

*Primary Examiner*—David Isabella
*Assistant Examiner*—Laura Fossum
*Attorney, Agent, or Firm*—Pravel, Hewitt, Kimball & Krieger

[57] ABSTRACT

A knee prosthesis includes a femoral prosthesis member having anterior, distal, and posterior articulating surface portions. The posterior articulating surface portions comprising a pair of condylar surface portions that are positioned at differing distances from the anterior non-articulating surface plane. The posterolateral articulating surface is a greater distance away from the anterior non-articulating surface than the posteromedial articulating surface. The femoral prosthesis has a non-articulating surface that includes a plurality of intersecting surfaces including at least distal, anterior, and posterior surfaces for receiving the patient's distal femur after it has been surgically prepared. A tibial component has concave articulating surfaces that receive the femoral component articulating surface portions during use. The angle of femoral rotation generally about the mechanical axis generally changes when going through a normal range of motion of the patient's knee while maintaining alignment of the femoral and tibial articular surfaces. The femoral prosthesis also has a proximal anterior region that is concave.

18 Claims, 5 Drawing Sheets

ASYMMETRIC FEMORAL PROSTHESIS

BACKGROUND OF THE INVENTION

1. Field of the Invention

The present invention relates to a medical prosthetic device and more particularly to an orthopedic medical prosthetic device. Even more particularly, the present invention relates to an improved asymmetric knee prosthesis and method of surgically implanting same wherein the prosthetic medial femoral condyles include a thinner medial posterior condyle and a thicker lateral posterior condyle, resulting in an elevation of the posterior medial femur joint line with the knee in flexion. The present invention also has a concave proximal anterior region.

2. General Background

Arthroplasty is the making of an artificial joint. In total knee arthroplasty there is a difficulty in reproducing the exact anatomy. The tibia is usually cut at ninety degrees (90°) to its axis in the frontal plane but the tibial plateau is at about eighty seven degree (87°). The disparity is due to the difficulty in accurately reproducing an eighty seven degrees (87°) cut. Also, it has been documented that with an eighty seven degrees (87°) or varus cut the tibial component has a tendency to loosen. (Proceedings of the Knee Society 1985–1986, Laskin, Varus Knee deformity). (Surgery of the Knee, Insall et al, 1993).

With a ninety degree (90°) cut, more bone is removed on the lateral side than on the medial side of the tibia. Neutral is defined as, parallel to a line tangent to the intact (not worn) posterior femoral condyles. When neutral femoral cuts are performed, and implants with equal medial and lateral thicknesses are used, there is a laxity of the lateral collateral ligament at ninety degrees (90°) of flexion. The lateral collateral ligament is lax in flexion because the resection of the tibia and the posterior resection of the femur are not parallel, but the prosthesis implanted has equal medial and lateral thicknesses on the tibial component and posterior condyles of the femoral component. This results in less space on the medial side and more space on the lateral side, which causes unbalanced ligaments.

The current solution to this problem is to rotate the cutting block so that more bone is removed from the posterior medial femoral condyle, this is referred to as external rotation. By externally rotating (clockwise rotation for a left knee when viewed from the distal end), the posterior femoral resection is parallel to the ninety degree (90°) tibial cut. This results in the collateral ligaments being balanced in extension and flexion when the prosthesis is implanted. The current industry standard is three degrees (3°) of external rotation which corresponds to the three degree (3°) difference between the eighty seven degree (87°) anatomical angle of the tibial plateau and the ninety degree (90°) angle of the tibial resection.

The benefits of this surgical procedure have been mentioned but there are some drawbacks. The femoral component is no longer aligned with the tibial component in full extension. The femoral component is rotated about three degrees (3°) with respect to the tibia when it is aligned parallel to the lateral plane. This malalignment potentially could cause increased wear of the tibial insert. A possible solution to this malalignment could be to externally rotate the tibial component, but this would result in reduced tibial coverage, which is not desired. Another possible solution may be to design the insert at an angle, but both turning the tibial tray externally or designing it into the insert have the problem of malalignment in flexion. With externally rotating the femoral component, there will be malalignment with the tibial insert either in flexion or extension whether the tibial tray or tibial insert is aligned straight or externally rotated.

A second problem with traditional external rotation is the chance of notching the lateral anterior femoral cortex. "Notching" occurs when more bone is removed anterolaterally than with the neutral resections resulting in a notch being created in the anterior cortex of the femur. Notching greatly increases the chances of the femur fracturing. A related problem to this is poor anteromedial implant coverage or even a gap between the implant and bone. In order to reduce the chances of notching anteriorly, the lateral side is placed flush with the cortex and a gap develops between the implant and bone anteromedially.

With external rotation, the patella tracking is altered. From zero degrees (0°) to ninety degrees (90°) of flexion benefits have been found because of lateralizing the patella in this flexion range. However, after ninety degrees (90°) of flexion, the patella will be medialized which can increase the lateral force and shear force on the patella. This can lead to higher stresses at the bone implant interface and lead to more wear of the patella implant on the patella.

Current femoral prosthesis have convex proximal anterior regions from a lateral view. This results in the patella and/or ligaments being displaced anteriorly. By having a concave anterior region, the patella and the ligaments are displaced anteriorly less because there is less metal in the concave region. This more closely resembles the anatomical femur and helps to improve patella tracking.

Another problem with traditional external rotation is the increased complexity and difficulty in instrumentation. The alignment of the cutting blocks must be variable and there is a different setup for left and right knees. Also, it can be difficult to accurately judge three degrees (3°) of external rotation when performing the surgery.

SUMMARY OF THE INVENTION

The objectives of the present invention are to balance the flexion and extension space, maintain proper alignment with the tibia, and to not notch the anterior femoral cortex when a ninety degree (90°) tibial resection and symmetric thickness tibial component is used.

The present invention provides an improved asymmetric femoral prosthesis for use in total knee arthroplasty.

The preferred embodiment includes a femoral prosthesis having anterior, distal, and posterior articulating surface portions. The posterior articulating surface portions include a pair of condylar surfaces that are positioned at differing distances from the anterior non-articulating or internal surface portion. The posterolateral articular surface is a greater distance from the anterior non-articulating surface than the posteromedial side.

The femoral prosthesis has an internal non-articulating surface that includes a plurality of surfaces for receiving a resected distal femur.

The tibial component includes concave articulating surfaces that receive the femoral component articulating surfaces during use.

The angle of femoral rotation generally about the mechanical axis gradually changes when going through a normal range of motion while maintaining alignment of the femoral and tibial articular surfaces. A gradual change is defined as a change that does not produce a step or immediate shift in the articular geometry. A normal range of motion that a patient would use could range from negative ten degrees (−10°) to one hundred thirty degrees (130°). During walking on a level surface a person would typically range from 0 degrees to 70 degrees. The entire movement associated with walking is referred to as gait. The range of motion required for going up stairs is about 0 to 60 degrees and to go down stairs is about 0 to 90 degrees. Getting up out of a chair can range from 0 to 90 degrees and deep knee bending could range from 0 to 130 degrees. Hyperextension, or a negative flexion could occur while standing of about 10 degrees.

In the preferred embodiment, the non-articulating surface includes distal, anterior and posterior surfaces as well as a pair of chamfer surfaces. Additional cut surfaces could be provided.

The posterior non-articulating surface defines a single plane that registers against a similarly configured resected surface of the distal femur. The present invention provides an improved method of implanting a femoral prosthesis on a patient's distal femur. The distal femur is first resected with a plurality of five cuts including anterior, posterior, distal and a pair of chamfer cuts. The femoral prosthesis is affixed to the patient's resected distal femur. The femoral prosthesis is an improved asymmetric prosthesis having anterior, posterior, and distal non-articulating portions that closely fit the anterior, posterior and distal cuts on the distal femur.

The patient's tibia is resected to receive a tibial prosthesis. The femoral and tibial cuts are generally parallel in full extension and relative to the tibial prosthesis and to the femoral prosthesis so that the angle of femur rotation generally about the patient's mechanical axis relative to the tibia gradually changes when going through a normal range of motion of the patient's knee from about minus twenty degrees (i.e. −20°) of flexion to about one hundred thirty degrees (130°) of flexion while maintaining alignment of the femoral and tibial articular surfaces.

The femoral posterior resections are made parallel to a line tangent to the intact posterior femoral condyles with approximately the same amount of bone being removed off of each posterior condyle, but the prosthesis has a thinner medial posterior condyle than its lateral posterior condyle. The distal thickness is the same between the medial and lateral condyles in the preferred embodiment. This results in balancing both the flexion and extension spaces similar to that of externally rotating a traditional femoral prosthesis.

The improved femoral prosthesis of the present invention solves the above discussed problems that have attended traditional femoral components aligned in neutral or external rotation.

The femoral prosthesis of the present invention aligns properly with the tibia in extension because it is not rotated like the externally rotated component. This results in improved femorotibial articulation and reduces the chance of severe wear. Since the tibial component is not externally rotated there is also not rotational incongruity between the femoral and tibial components in flexion.

The anterolateral cortex should not be notched because no additional bone is removed. Neutral cuts are used which do not notch the anterior femur. There is improved anterior medial bone coverage because the prosthesis is not rotated (there is no gap on the anteromedial side).

The instruments for putting in the new femoral component are simpler to use because the same procedure is used for a right or left knee and the work of positioning the three degree (3°) resection is eliminated.

The design described is the preferred design but it is not the only way to accomplish the same goal. An alternative method and apparatus uses a ninety degree (90°) tibial resection and a tibial component that is thicker on the lateral side than the medial side. The femoral component provides a thinner lateral distal condyle than the medial distal condyle. The posterior condyles are of equal thickness at about ninety degrees (90°) of flexion in the alternate embodiment.

With the present invention the thickness could be altered both distally and posteriorly, simply by making an angled distal resection in the frontal plane or making an angled posterior resection with respect to neutral rotation. If the anterior resection was made neutral and the posterior resection was rotated then the cross section from anterior to posterior would be trapezoidal in shape.

Differences between the positions of the medial and lateral articular surfaces are independent of the box geometry and any variation of distal or posterior condyle thickness. The distal or posterior cuts could be made at an angle or at different levels in order to produce the same design objective but maintain constant condyle thicknesses or to maintain different condyle thicknesses. This would produce the same results of balancing the flexion and extension spaces, with proper alignment with the tibia, and have different thicknesses than in the description of this new femoral prosthesis.

The femoral component could also be designed with more or less external rotation incorporated. With traditional neutral resections of the distal and posterior femur, in order to design for more external rotation there would be a larger difference in the thickness of the posterior condyles with the preferred embodiment. The medial posterior condyle is thinner than the lateral posterior condyle of the femoral component so that at ninety degrees (90°) of flexion the femoral joint line is angled at three (3°) of rotation along its mechanical axis. Other angles could be designed into the femoral ranging from about one degree (1°) to ten degrees (10°) at about ninety degrees (90°) of flexion. The articular geometry of the condyles changes such that the femoral component articulates with the tibial component during flexion and extension without requiring the femoral component to turn relative to the alignment of the tibial insert in the transverse plane.

The new asymmetric femoral also has a concave proximal anterior region in a lateral view. This results in the femoral component being thinner in this region. The benefits are that the thickness of the implant more closely matches the thickness of the bone that is removed. The patella and the ligaments can function more anatomically because extra metal is not being added to the anterior cortex of the femur. The concave region has an arc center that is located anterior to the component where a convex region would have an arc center that is posterior to the anterior surface of the component.

BRIEF DESCRIPTION OF THE DRAWINGS

For a further understanding of the nature and objects of the present invention, reference should be had to the following detailed description, taken in conjunction with the accompanying drawings, in which like parts are given like reference numerals, and wherein.

DETAILED DESCRIPTION OF THE PREFERRED EMBODIMENT

Figure 1:
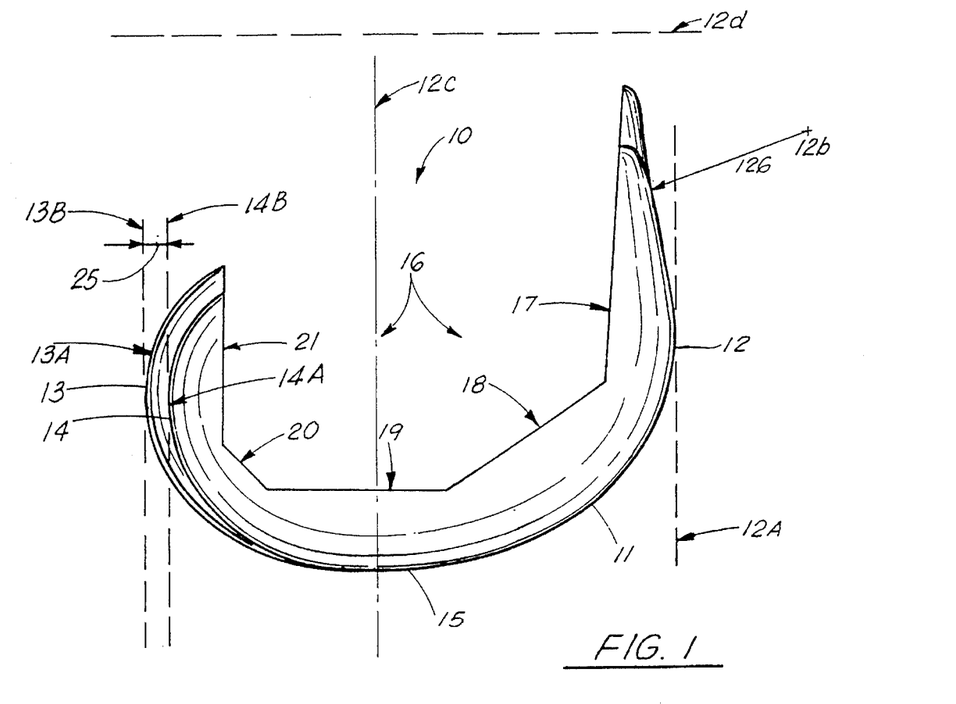
FIG. 1 is a lateral view of the preferred embodiment of the present invention showing the medial and lateral posterior condyle thickness and the concave anterior region.
Figure 2:
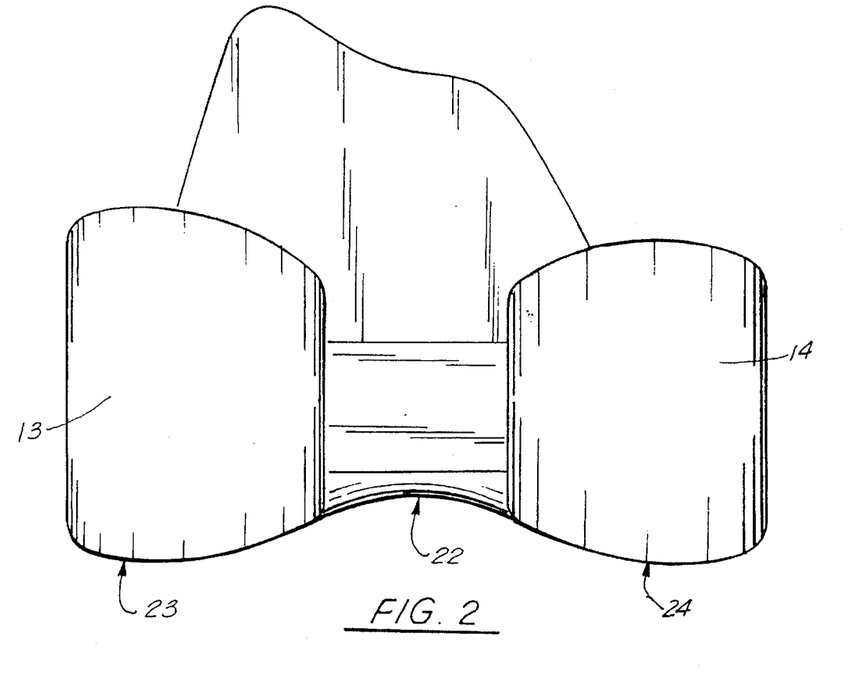
FIG. 2 is a frontal view of the preferred embodiment of the apparatus of the present invention.

FIGS. 1 and 2 show generally the preferred embodiment of the apparatus of the present invention designated generally by the numeral 10. The asymmetric femoral component 10 includes a prosthesis articulating surface 11 that includes an anterior articulating surface portion 12, distal articulating surface 15, and a pair of condylar surfaces including lateral posterior condyle 13 having posterior condylar surface 13A and medial posterior surface condyle 14 having posterior condylar surface 14A.

The proximal side of asymmetric femoral prosthesis 10 provides a recess 16 that receives a patient's distal femur after the distal femur has been resected to fit the plurality of surfaces 17–21. Anterior proximal surface 17 is a generally flat surface that intersects proximal anterior chamfer 18. Anterior chamfer 18 extends between anterior proximal surface 17 and proximal surface 19. Proximal posterior chamfer 20 extends between surface 19 and posterior proximal surface 21. In FIG. 2, asymmetric femoral prosthesis 10 has a central recess portion 22 between lateral distal surface 23 and medial distal surface 24.

In FIG. 1, there can be seen a difference in the position between the surfaces 13A–14A. A line drawn tangent to the most posterior portion of lateral posterior condyle 13, generally parallel to the frontal plane, is defined by the line 13B. A line drawn tangent to the most posterior point on posterior condylar surface 14A (generally parallel to frontal plane) is the line 14B. A distance 25 between the lines 13B and 14B shows that the lateral posterior condyle 13 is thicker than the medial posterior condyle 14 whereas the inner surface 21 of each of the condyles 13 and 14 is the same flat surface 21, defining a plane that accepts corresponding resected surfaces on the patient's distal femur. The frontal plane or coronal plane is shown in FIG. 1 as a plane going through line 12C and perpendicular to the page. It is a plane that splits the body into a front and a rear half. The transverse plane is typically a plane that goes through the waist area and cuts the body into a top and a bottom half. For ease of use it is shown in FIG. 1 as a plane going through line 12d and perpendicular to the page. This plane is parallel to the typical transverse plane and for this description is functionally the same.

This femoral component 10 essentially has three degrees (3°) of external rotation built into it. This is in contrast to the current procedure of the surgeon cutting the femur at three degrees (3°) of external rotation. On the femoral component 10 of the present invention, the angle of femoral rotation generally about the mechanical axis 32 gradually changes when going through a normal range of motion of the patient's knee, typically from about zero degrees (0°) of flexion to about ninety (90°) to one hundred thirty degrees (130°) of flexion. A normal range of motion that a patient would use could range from negative ten degrees (−10°) to one hundred thirty (130°) degrees. During walking on a level surface a person would typically range from 0 degrees to 70 degrees. The entire movement associated with walking is referred to as gait. The range of motion required for going up stairs is about 0 to 60 degrees and to go down stairs is about 0 to 90 degrees. Getting up out of a chair can range from 0 to 90 degrees and deep knee bending could range from 0 to 130 degrees. Hyperextension, or a negative flexion could occur while standing of about 10 degrees. The rotation balances the flexion gap between the femoral and tibial components as well as aligning the femoral component articular surface parallel to the lateral plane in flexion and extension. The three degrees (3°) of external rotation is generally along the mechanical axis 32 of the femur.

Figure 4:
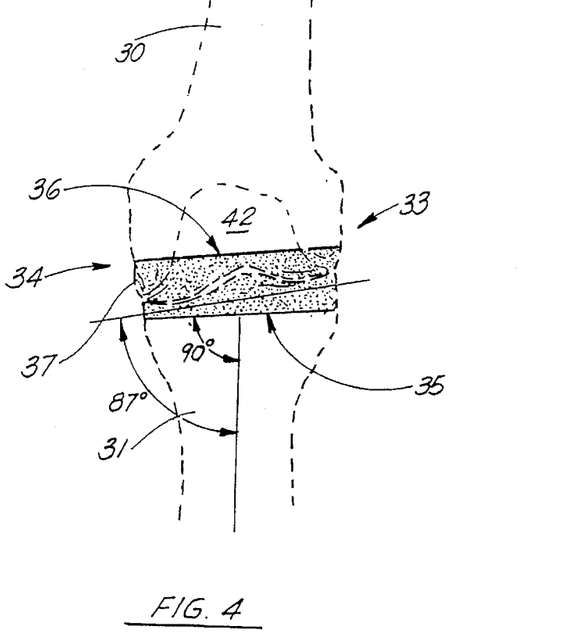
FIG. 4 is a frontal view of a human knee joint showing a ninety degree (90°) tibia resection and a parallel femoral distal resection.
Figure 5:
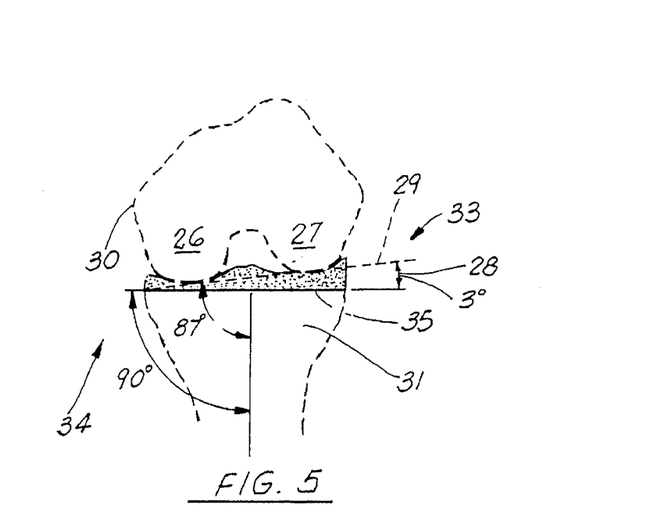
FIG. 5 is a frontal view of a human knee joint in ninety degree (90°) flexion illustrating the anatomical angle of the tibia at eighty seven degree (87°) and the tibial resection at ninety degrees (90°)

In total knee arthroplasty there is a difficulty in reproducing the exact anatomy. As illustrated in FIGS. 4 and 5, the patient's tibia 31 is usually cut at ninety degrees (90°) to its axis in the frontal plane but the tibial plateau is at eighty seven degrees (87°). The disparity is due to the difficulty in accurately reproducing an eighty seven degree (87°) cut. Also, it has been documented that with an eighty seven degree (87°) or varus cut the tibial component has a tendency to loosen. (Proceedings of the Knee Society 1985–1986, Laskin, Varus Knee deformities).

Figure 3:
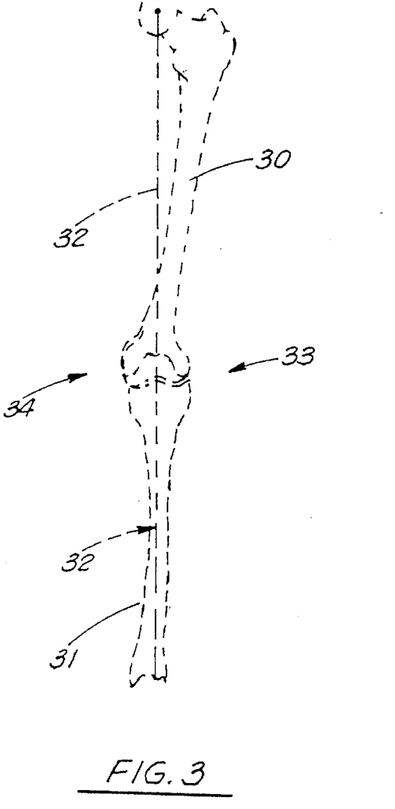
FIG. 3 is a frontal view illustrating human femur, knee joint, and tibia and the leg mechanical axis.
Figure 7:
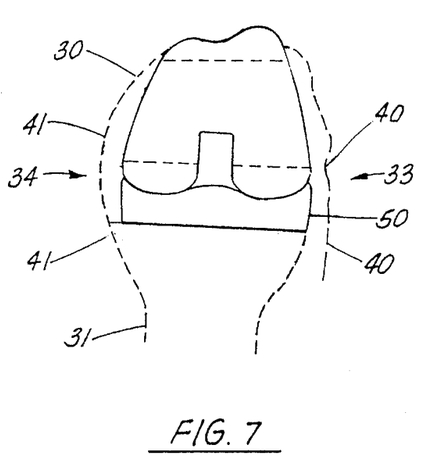
FIG. 7 is a frontal view of a human knee joint in ninety degrees (90°) of flexion showing a symmetric thickness tibial and femoral prosthesis in neutral alignment.

With a ninety degree (90°) cut, more bone is removed on the lateral side 33 than on the medial side 34 of the tibia 31 as shown in FIGS. 3, 4, and 5. In FIG. 4, the tibial cut is designated as 35. Because of this, at ninety degrees (90°) of flexion, when neutral femoral cuts are performed the resection 35 of the tibia and the posterior resections 38 and 39 of the femur are not parallel. This results in less space on the medial side 34 and more space on the lateral side 33, which causes unbalanced ligaments 40 and 41 when traditional tibial and femoral components are used that have symmetric thicknesses on the medial and lateral sides (see FIG. 7).

Figure 8:
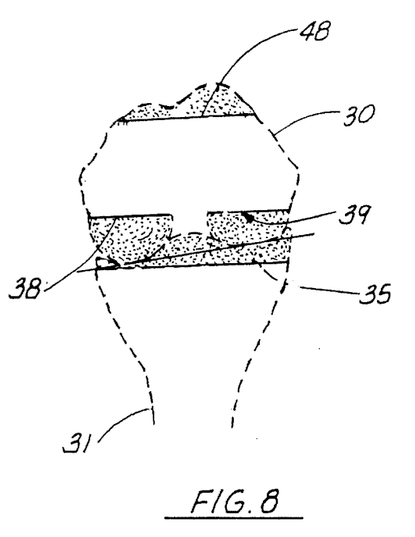
FIG. 8 is a frontal view of a human knee joint illustrating externally rotated resections on the anterior and posterior femur and showing more bone cut from the anterolateral femur and from the posteromedial femur.
Figure 9:
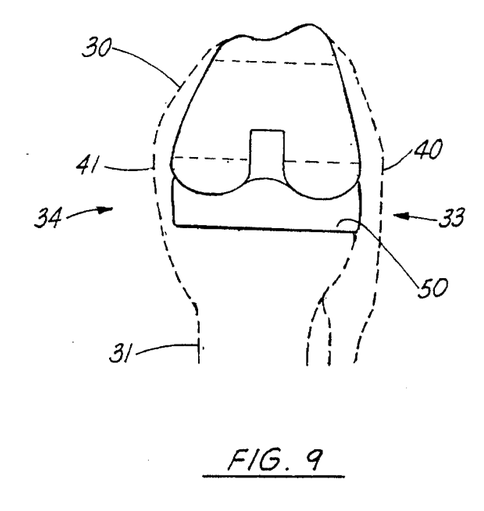
FIG. 9 is a frontal view of a knee joint in ninety degrees (90°) of flexion with a symmetric thickness tibial and femoral prosthesis externally rotated and the balanced collateral ligaments.

The current solution to this problem is to rotate the cutting block so that more bone is removed from the posteromedial femoral condyle. This is referred to in the art as external rotation. By externally rotating (clockwise rotation for a left knee when viewed from the distal end), the posterior femoral resection is parallel to the ninety degree (90°) tibial cut (see FIG. 8). This results in the collateral ligaments 40 and 41 being balanced in extension and flexion when the prosthesis is implanted as shown in FIG. 9. The current industry standard is three degrees (3°) of external rotation.

Figure 6:
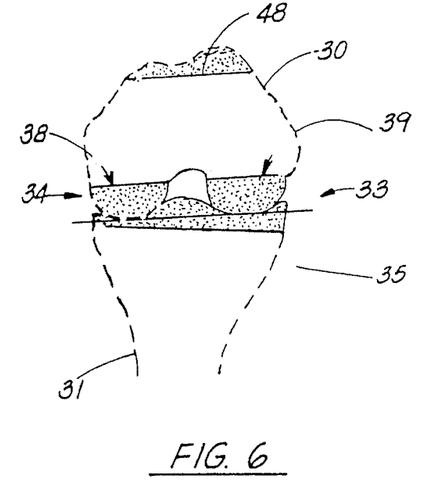
FIG. 6 is a frontal view of a human knee joint in ninety degrees (90°) of flexion illustrating neutral femoral posterior and anterior resections with a ninety degree (90°) tibial resection.
Figure 10:
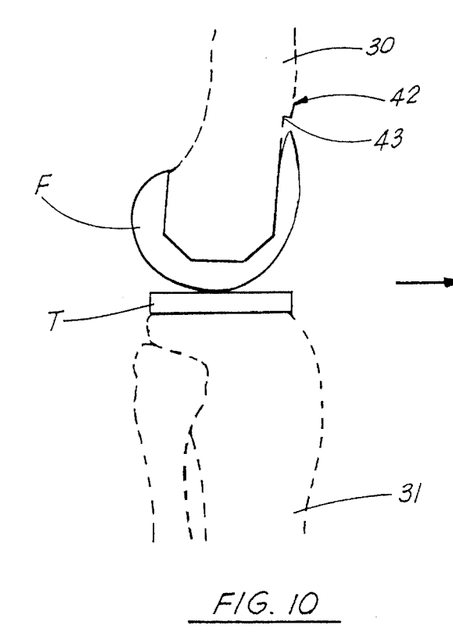
FIG. 10 is a lateral view illustrating a femur that has been notched in the anterior cortex as part of a prior art knee joint replacement surgical procedure.

One problem with traditional external rotation is the chance of notching the anterolateral femoral cortex as illustrated in FIG. 10 with prior art femoral prosthesis F and tibial prosthesis T. FIG. 8 shows that more bone is removed anterolateral and posteromedial than with the femoral neutral resections shown in FIG. 6. FIG. 10 illustrates the anterior cortex 42 with a notch 43, which greatly increases the chance of the femur fracturing.

Figure 11:
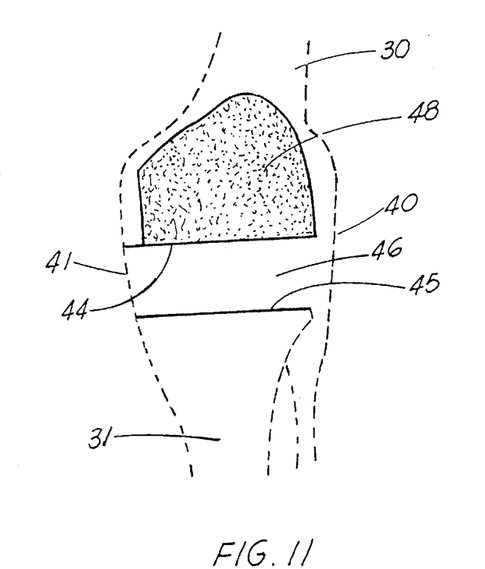
FIG. 11 illustrates knee joint resections using the method of the present invention and showing the extension space parallel.
Figure 12:
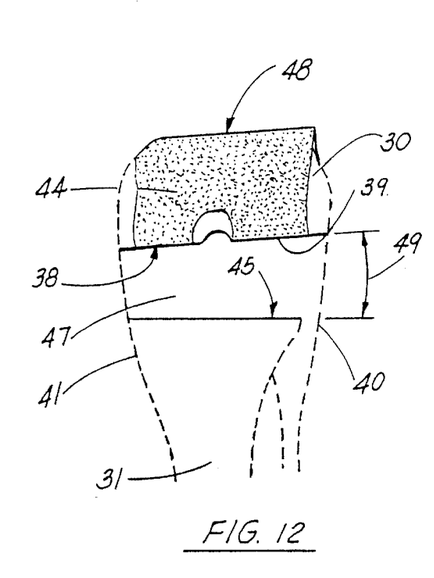
FIG. 12 illustrates the neutral femoral resections using the method of the present invention, showing the flexion space that is trapezoidally shaped.
Figure 13:
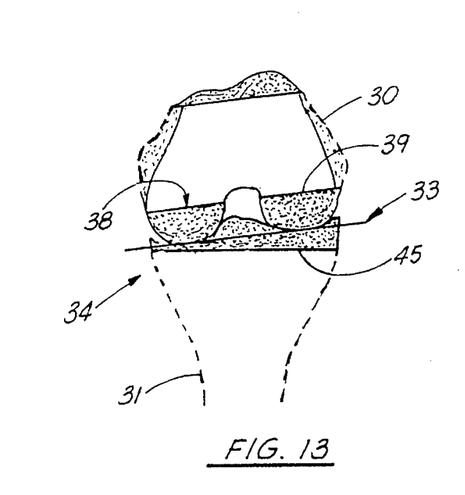
FIG. 13 is a frontal view of a knee joint in ninety degrees (90°) of flexion showing neutral femoral resections of the anterior cortex and posterior condyles.
Figure 14:
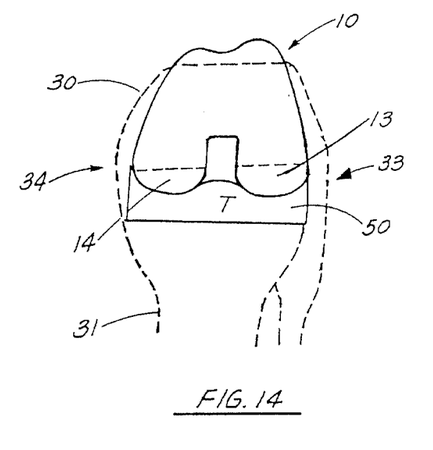
FIG. 14 is a frontal view of the preferred embodiment of the present invention of a knee joint ninety degrees (90°) in flexion showing a thinner posteromedial condyle than the posterolateral and balanced collateral ligaments.
Figure 15:
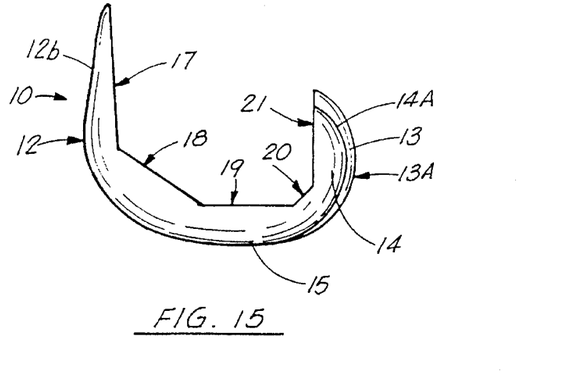
FIG. 15 is a lateral view of the preferred embodiment of the asymmetric component of the present invention showing the different medial and lateral curves posteriorly.

In the preferred embodiment, the femoral posterior resections are made neutral with approximately the same amount of bone being removed off of each posterior condyle, but the prosthesis has a thinner medial posterior condyle 14 than its lateral posterior condyle 13 as seen in FIG. 14. The distal thickness is the same between the medial and lateral condyles in the preferred embodiment as shown in FIG. 15. This results in balancing both the flexion and extension spaces similar to that of externally rotating a traditional femoral prosthesis. FIGS. 11 and 12 show neutral femoral resections as used in the method of the present invention. The distal femoral resection is indicated as 44, the tibial resection as 45, defining a parallel extension space 46. The anterior resection is indicated as 48 in FIGS. 11 and 12. In FIG. 12, posterior femoral resections 38 and 39 appear when the knee is in flexion, defining a trapezoidal flexion space 47.

Figure 16:
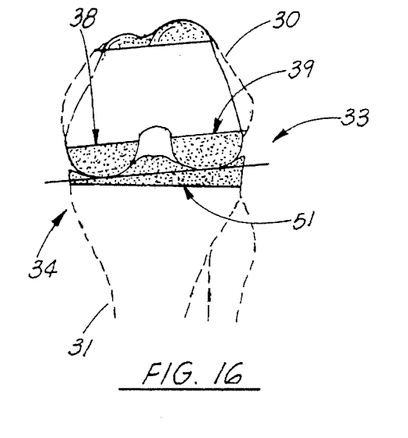
FIG. 16 is a frontal view of a knee in ninety degree (90°) of flexion of an alternate embodiment of the method and apparatus of the present invention showing neutral femoral resections.
Figure 17:
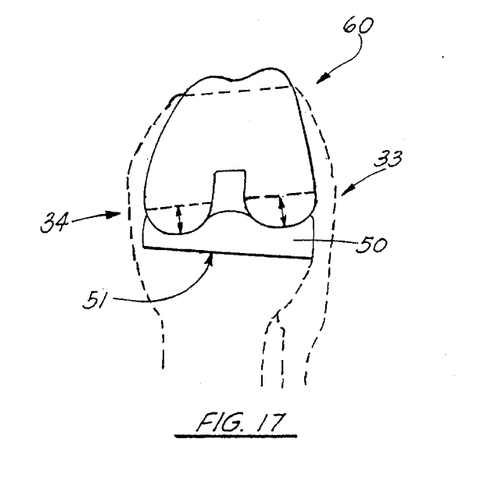
FIG. 17 is a frontal view of a knee joint in ninety degrees (90°) of flexion showing the alternate embodiment of the apparatus of the present invention with a tibial component that has a thicker lateral section that it's medial section.
Figure 18:
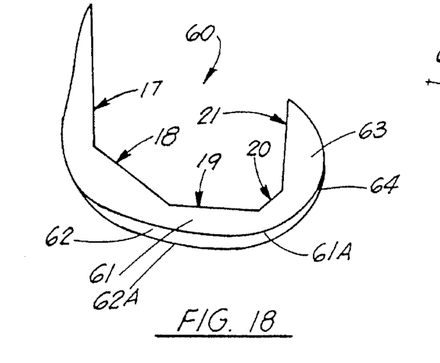
FIG. 18 is a lateral view of the alternate embodiment of the asymmetric femoral component of the present invention showing the different medial and lateral curves distally.

An alternative method and apparatus is shown in FIGS. 16–18. The alternate embodiment of the method and apparatus of the present invention uses a ninety degree (90°) tibial resection 51 and a tibial component 50 that is thicker on the lateral side than the medial side. The femoral component 60 would then have a thinner lateral distal condyle 61 than the medial distal condyle 62. The posterior condyles 63 and 64 would then have the same thickness at about ninety degrees (90°) of flexion in the alternate embodiment.

With the present invention the thickness could be altered both distally and posteriorly simply by making an angled distal resection in the frontal plane or making an angled posterior resection with respect to neutral rotation. If the anterior resection was made neutral and the posterior resection was angled then the cross section from anterior to posterior would be trapezoidal in shape in the transverse plane.

The asymmetric femoral prosthesis components 10 and 60 shown in FIGS. 13–18 show that the difference between the medial and lateral sides is independent of the box geometry and any variation of distal or posterior condyle thickness. The distal or posterior cuts could be made at an angle or at different levels in order to produce the same design objective but maintain constant condyle thicknesses or to maintain different condyle thicknesses. This would produce the same results of balancing the flexion and extension spaces, with proper alignment with the tibia, and have different thicknesses in the condyles than in the description of this new femoral prosthesis.

The femoral component could also be designed with more or less external rotation built in. With traditional neutral resections of the distal and posterior femur, there would be a larger difference in the thickness of the posterior prosthesis condyles to produce more external rotation.

The new femoral component design is intended to be placed to compensate for a ninety degree (90°) tibial resection. Resecting the tibia at ninety degrees (90°) in the frontal plane and placing a prosthetic tibial component, which has the same thickness medially and laterally, results in an elevated medial compartment of the tibia. To compensate for this, the femoral component of the present invention, in conjunction with the resections of the distal and posterior femur, elevate the medial joint line relative to the femur to compensate for the elevation that occurs in the tibia.

On the posterior femur, this is accomplished by resecting the posterior femur roughly parallel to the posterior femoral condyle joint line. The prosthetic medial femoral condyle is thinner than the resection that occurs medially. This results in an elevation of the posterior medial femoral joint line with the knee in flexion.

The distal resection of the femur is accomplished by removing asymmetrical amounts of bone from the medial and lateral condyles of the femur. The distal medial and lateral surfaces are then replaced with equal thicknesses of prosthetic medial and lateral surfaces. Because additional bone has been removed from the medial distal femoral condyle, this results in an elevation of the medial distal femoral joint line with the knee in extension. This too compensates for elevation of the medial compartment of the tibial that occurs due to the ninety degree (90°) tibial resection in the frontal plane.

Figure 19:
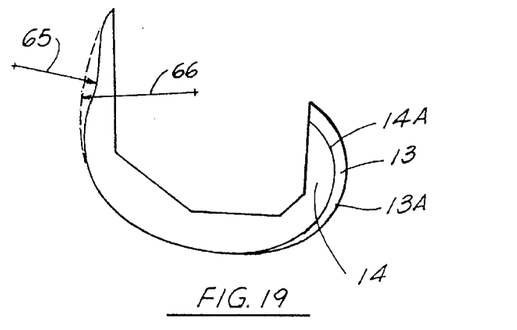
FIG. 19 is a lateral view of a femoral component showing both the traditional convex anterior and the concave anterior region.

FIG. 19 shows a lateral view of a femoral component. The anterior region 65 shows the concave region of the new femoral where the arc center is located anterior to the component. The anterior region 66 shows the convex region of a traditional femoral component where the arc center is located posterior to the anterior surface. The concave anterior results in less metal anteriorly as shown in FIG. 19 which more closely replaces the resected bone with the same amount of metal.

The following table lists the parts numbers and parts descriptions as used herein and in the drawings attached hereto.

PARTS LIST

| Part Number | Description |
| --- | --- |
| 10 | asymmetrical femoral prosthesis |
| 11 | prosthesis articulating surface |
| 12 | anterior articulating surface |
| 12A | anterior tangent line |
| 12B | anterior concave surface |
| 12C | frontal plane |
| 12D | transverse plane |
| 13 | lateral posterior condyle |
| 13A | posterior condylar surface |
| 13B | posterolateral tangent line |
| 14 | medial posterior condyle |
| 14A | posterior condylar surface |
| 14B | posteromedial tangent line |
| 15 | distal surface |
| 16 | proximal recess |
| 17 | anterior proximal surface |
| 18 | proximal anterior chamfer |
| 19 | proximal surface |
| 20 | proximal posterior chamfer |
| 21 | posterior proximal surface |
| 22 | recess |
| 23 | lateral distal surface |
| 24 | medial distal surface |
| 25 | offset distance |
| 26 | medial distal surface |
| 27 | lateral distal surface |
| 28 | angle |
| 29 | anatomical angle tibia |
| 30 | femur |
| 31 | tibia |
| 32 | mechanical axis |
| 33 | lateral side |
| 34 | medial side |
| 35 | ninety degree tibial resection |
| 36 | distal femoral resection |
| 37 | extension space |
| 38 | femoral resection - posteromedial |
| 39 | femoral resection - posterolateral |
| 40 | lateral collateral ligament |
| 41 | medial collateral ligament |
| 42 | anterior femoral cortex |
| 43 | notch |
| 44 | distal femoral resection |
| 45 | ninety degree tibial resection |
| 46 | extension space - parallel |
| 47 | flexion space - trapezoidal |
| 48 | anterior resection |
| 49 | angle |
| 50 | tibial component |
| 51 | tibial resection |
| F | femoral prosthesis |
| T | tibial prosthesis |
| 60 | femoral component |
| 61 | lateral distal condyle |
| 61A | lateral distal surface |
| 62 | medial distal condyle |
| 62A | medial distal surface |
| 63 | posterolateral condyle |
| 64 | posteromedial condyle |
| 65 | concave anterior region of new asymmetric femoral |
| 66 | convex anterior region of traditional femoral |

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. A knee prosthesis for replacing a patient's knee having a mechanical axis defined by a line drawn between the femoral head and the central region of the femoral knee end of the patient, comprising:

a) a femoral prosthesis having internal anterior, posterior and distal non-articulating surface portions;

b) said femoral prosthesis having distal and posterior articulating surface portions, the posterior articulating surface portions comprising lateral and medial condylar surface portions that are positioned at differing distances from said anterior non-articulating surface portion wherein the lateral condylar surface portion is spaced farther from said anterior non-articulating surface portion than the medial condylar surface portion;

c) a tibial component having concave articulating surfaces that receive the femoral prosthesis articulating surface portions during use;

d) the femoral articulating surface portions and the tibial articulating surfaces being shaped to define an angle of femoral rotation about the mechanical axis of the patient's leg; and e) wherein said angle of femoral rotation about the mechanical axis gradually changes when going through a normal range of motion of the patient's knee.

2. The knee prosthesis of claim 1 wherein the non-articulating surfaces comprise a plurality of intersecting surfaces.

3. The knee prosthesis of claim 2 wherein the posterior non-articulating surface defines a single plane.

4. The knee prosthesis of claim 1 wherein the non-articulating surfaces comprise flat intersecting planes.

5. The knee prosthesis of claim 1 further comprising an anterior articulating surface.

6. The knee prosthesis of claim 5 wherein the anterior non-articulating surface is substantially flat and forms an angle of at least ninety degrees with the distal non-articulating surface.

7. The knee prosthesis of claim 2 wherein the posterior non-articulating surface is substantially flat and forms an angle of at least ninety degrees with the distal non-articulating surface.

8. The knee prosthesis of claim 1 wherein the angle of femoral rotation about the mechanical axis gradually changes when going through a range of motion from about zero degrees of flexion to about ninety degrees (90°) of flexion.

9. The knee prosthesis of claim 1 wherein the angle of femoral rotation about the mechanical axis gradually changes when going through a range of motion from about zero degrees of flexion to about one hundred thirty degrees (130°) of flexion.

10. The knee prosthesis of claim 1 wherein the angle of femoral rotation about the mechanical axis gradually changes when going through a range of motion from about negative twenty degrees (−20°) of flexion to about ninety degrees (90°) of flexion.

11. The knee prosthesis of claim 1 wherein the angle of femoral rotation about the mechanical axis gradually changes when going through a range of motion from about negative twenty degrees (−20°) of flexion to about one hundred forty degrees (140°) of flexion.

12. The knee prosthesis of claim 1 wherein the angle of femoral rotation about the mechanical axis gradually changes when going through a range of motion from about twenty degrees (20°) of flexion to about eighty degrees (80°) of flexion.

13. The knee prosthesis of claim 1 wherein the angle of femoral rotation about the mechanical axis gradually changes when going through a range of motion of about sixty degrees (60°).

14. The knee prosthesis of claim 1 wherein the angle of femoral rotation about the mechanical axis. gradually changes when going through a range of motion of about eighty degrees (80°).

15. A knee prosthesis for replacing a patient's knee having a mechanical axis defined by a line drawn between the femoral head and the central region of the femoral knee end of the patient, comprising:

a) a femoral prosthesis having distal and posterior articulating surface portions;
   b) the femoral prosthesis having an internal distal non-articulating surface and an internal posterior non-articulating surface;
   c) the femoral prosthesis including medial and lateral posterior condylar portions that have different thicknesses measured respectively from the posterior non-articulating surface to the posterior articulating surface portion at the respective posterior condylar portions, the thickness of the posterior lateral condylar portion being greater than the thickness of the posterior medial condylar portion;
   d) a tibial component having concave articulating surfaces that receive the femoral prosthesis articulating surface portions during use;
   e) the femoral articulating surface portions and the tibial articulating surfaces being shaped to define an angle of femoral rotation about the mechanical axis of the patient's leg; and
   f) wherein said angle of femoral rotation about the mechanical axis gradually changes when going through a normal range of motion of the patient's knee.

16. The knee prosthesis of claim 15 wherein the non-articulating surface comprises a plurality of intersecting surfaces including at least distal and posterior surfaces.

17. The knee prosthesis of claim 15 wherein the angle of femoral rotation about the mechanical axis gradually changes when going through a range of motion of about sixty degrees (60°).

18. The knee prosthesis of claim 15 wherein the angle of femoral rotation about the mechanical axis gradually changes when going through a range of motion of about ninety degrees (90°).

* * * * *